(12) United States Patent
Zhang et al.

(10) Patent No.: US 8,115,973 B2
(45) Date of Patent: Feb. 14, 2012

(54) IMAGING APPARATUS FOR FULLY AUTOMATIC SCREEN PRINTER

(75) Inventors: Xianmin Zhang, Guangzhou (CN); Yongcong Kuang, Guangzhou (CN); Yuequan Tang, Dongguan (CN)

(73) Assignee: South China University of Technology (CN)

( * ) Notice: Subject to any disclaimer, the term of this patent is extended or adjusted under 35 U.S.C. 154(b) by 1194 days.

(21) Appl. No.: 11/836,497

(22) Filed: Aug. 9, 2007

(65) Prior Publication Data

US 2008/0130068 A1    Jun. 5, 2008

(30) Foreign Application Priority Data

Nov. 30, 2006  (CN) .......................... 2006 1 0123893
Nov. 30, 2006  (CN) .......................... 2006 1 0123894

(51) Int. Cl.
*H04N 1/04* (2006.01)
*H04N 1/42* (2006.01)

(52) U.S. Cl. ....... 358/474; 358/483; 358/1.15; 358/476; 358/481; 228/39; 101/128

(58) Field of Classification Search .................. 358/483, 358/474, 1.15, 481, 476; 228/39; 101/128
See application file for complete search history.

(56) References Cited

U.S. PATENT DOCUMENTS

| | | | | |
|---|---|---|---|---|
| 6,123,024 A | * | 9/2000 | Williams et al. | 101/129 |
| 2007/0102478 A1 | * | 5/2007 | Prince | 228/39 |

* cited by examiner

*Primary Examiner* — David K. Moore
*Assistant Examiner* — Quang N Vo
(74) *Attorney, Agent, or Firm* — Seyfarth Shaw LLP

(57) ABSTRACT

An imaging apparatus for fully automatic screen printer including two stacked light sources, two stacked beamsplitters, two stacked optical reflectors, two stacked imaging lens and two stacked image sensors, wherein the two stacked optical reflectors and the two stacked light sources are correspondingly disposed on two different sides of the two beamsplitters, the two stacked imaging lens are disposed on another side of the beamsplitters different from that of the optical reflectors and the light sources, the two stacked image sensors are disposed behind the imaging lens; the optical reflectors are provided with an upward reflection plane and a downward reflection plane, the optical axes of the imaging lenses are orthogonal to that of the light sources. The imaging apparatus is of two independent optical paths which capture the image of the printed circuit board and that of the screen respectively. Furthermore, the imaging apparatus is of compact structure, high acquiring speed and optical paths easy to be adjusted.

11 Claims, 4 Drawing Sheets

IMAGING APPARATUS FOR FULLY AUTOMATIC SCREEN PRINTER

BACKGROUND OF THE INVENTION

The present invention relates to an imaging apparatus, specially relates to an imaging apparatus for the reference mark measurement and inspecting the paste solder printing; more specially relates to an imaging apparatus for the reference mark measurement of the screen and the printed circuit board during the paste solder printing of the printed circuit board of the screen printing process, and for the inspection of the screen and the printed circuit board during the paste solder printing.

During the paste solder printing of the printed circuit board of the screen printing process, in order to apply the solder paste to the printed circuit board accurately, the portions of the printed circuit board desired to be printed are required to be corresponding to the holes of the screen. Reference mark measurement is usually used for the alignment of the screen and the printed circuit board, that is to say, signs are marked on both the screen and the printed circuit board so as to ensure that the portions of the printed circuit board desired to be printed are corresponding to the holes of the screen when the relevant signs of the screen are calibrated with respect to that of the printed circuit board. The simplest method of the alignment is mechanical positioning, in which the reference marks are the holes formed on the printed circuit board, and the sinker bars of the pistons of one or more cylinder-piston means are inserted into the positioning holes of the printed circuit board when positioning. However, this method is of the defects including low precision, low speed and even that there is no positioning hole due to the different positioning aperture of different printed circuit board. Therefore, this method is difficult to adapt to the development of the SMT production with high density, large output and high precision, and will fall into disuse gradually.

With the development of the electronic component in the direction of micromation, chip type and high density, the screen printer is required to be of higher precision, speed and reliability. Currently, in the SMT product line of the printed circuit board with high density, most of the defects come from the printing faults of the solder paste. The quality inspection of the solder-paste printing is mainly carried out by manual inspection. The manual inspection may have the problems including strong subjectivity, poor reproducibility, misjudgment and overlook due to vision fatigue, etc. The manual inspection is hardly qualified for the inspection requirement of SMT product line.

A screen printer utilizing machine vision technique can realize simultaneously both alignment with respect to the reference mark in high speed and high precision, and printing quality inspection during printing. At present, the imaging apparatus of the screen printer of this type normally includes a low-angle ring light source, two light sources, a beamsplitter, an optical reflector, an imaging lens and an image sensor. During the operation, the two light sources on different horizontal planes illuminate at different time, the light sources irradiate on the screen or the printed circuit board through the beamsplitter, and then the beams of light are reflected back to the beamsplitter and refracted to the imaging lens by the beamsplitter, and finally imaging on the image sensor is obtained. This method is of the advantages including simple light path and low cost. However, acquiring the images at different time may result in that the image acquiring positions of the lower image and the upper image are inconsistent; and the dimension of the imaging apparatus in the direction of the upward and downward light path is too large, so that the distance between the printed circuit board and the screen is accordingly large when acquiring the image.

SUMMARY OF THE INVENTION

An object of the present invention is to provide an imaging apparatus with compact structure, in which the light path is easy to adjust and the images can be acquired from the same position in upward and downward directions. The imaging apparatus is used for image acquiring during the reference mark measurement of the screen and the printed circuit board, and during the inspection in the solder-paste printing process.

The above object of the present invention is achieved by the following technical solutions:

An imaging apparatus for fully automatic screen printer including two stacked light sources, two stacked beamsplitters, two stacked optical reflectors, two stacked imaging lens and two stacked image sensors, wherein the two stacked optical reflectors and the two stacked light sources are correspondingly disposed on two different sides of the two beamsplitters, the two stacked imaging lens are disposed on another side of the beamsplitters different from that of the optical reflectors and the light sources, the two stacked image sensors are disposed behind the imaging lens; the optical reflectors are provided with an upward reflection plane and a downward reflection plane, the optical axes of the imaging lenses are orthogonal to that of the light sources.

Preferably, the two stacked optical reflectors and the two stacked light sources are disposed on two opposite sides of the two beamsplitters, the imaging apparatus forms a T-shaped structure.

Preferably, the two stacked optical reflectors and the stacked imaging lens are correspondingly disposed on two opposite sides of the two stacked beamsplitters, the two stacked light sources are disposed on another side of the two stacked beamsplitters different from that of the optical reflectors and the imaging lens, the imaging apparatus forms a L-shaped structure.

Preferably, the angles of the light-splitting planes of the beamsplitters with respect to the axes of the imaging lenses and the axes of the light source are both 45°.

Preferably, the beamsplitter may be formed of two right angular prisms; or the beamsplitter may be formed of one or two light-splitting plates.

Preferably, the optical reflector may be formed of an isosceles right angle prism or two reflection lens or a right angle prism with two reflection planes.

Preferably, the image sensor may be formed of an analog or digital CCD camera or CMOS camera.

Preferably, the imaging apparatus further includes a ring light source, the ring light source is formed of a LED ring light source between a printed circuit board and the optical reflector in order to provide lateral illumination for the printed circuit board, the beam of light reflected downwards by the optical reflector travels through the central hole of the ring light source and then irradiates on the printed circuit board.

Preferably, the light source and the image sensor are connected to the camera controller of the image acquiring control and processing device so as to control the switching of the light source and accordingly control the image acquiring of the screen and the printed circuit board; the video signal output end of the image sensor is connected to the image acquiring card of the image acquiring control and processing device, so as to convert the acquired image video signals into digital signals.

THE ADVANTAGES OF THE PRESENT INVENTION

The imaging apparatus according to the present invention can simultaneously capture the images in downward direction (i.e. the screen) and upward direction (i.e. the printed circuit board), so that the relative movement of the printed circuit board and the screen is minimized. Moreover, the combination of the coaxial illumination and the side illumination can improve the quality of the reference mark image of the printed circuit board and the inspection image of the solder paste, which adapts to the image acquiring during the reference mark measurement of the screen and the printed circuit board, and during the inspection in the solder-paste printing process.

Figure 1:
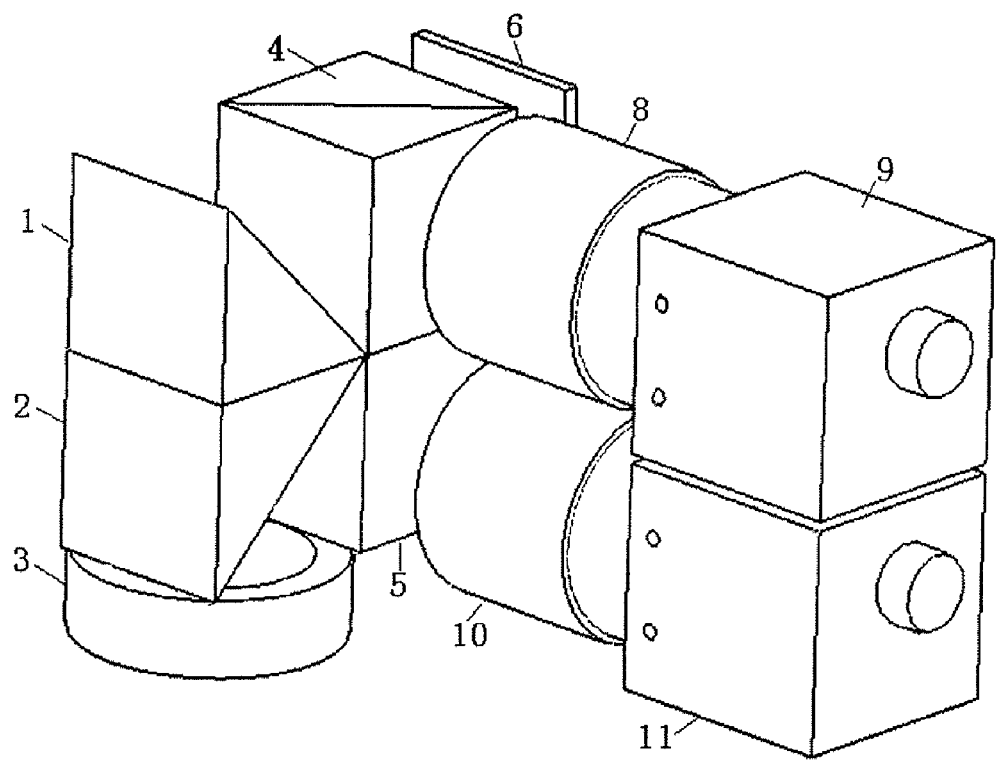
FIG. 1 is a schematic perspective view of the first embodiment showing a T-type imaging apparatus with two lenses for fully automatic screen printer.
Figure 2:
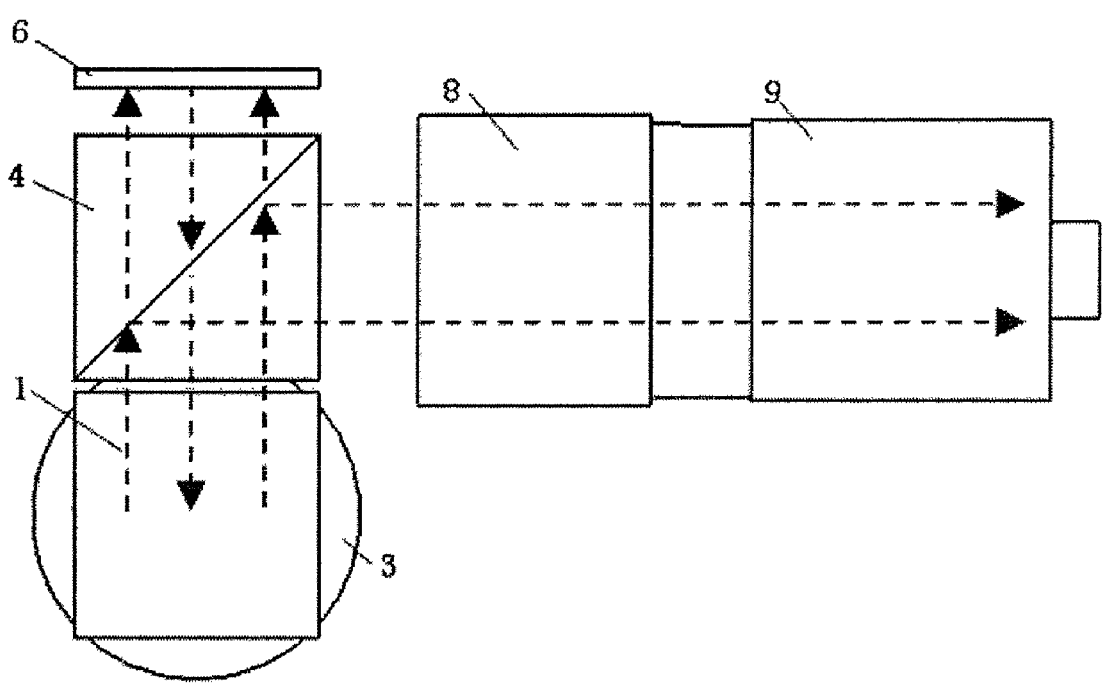
FIG. 2 is the top view of the imaging apparatus shown in FIG. 1.
Figure 3:
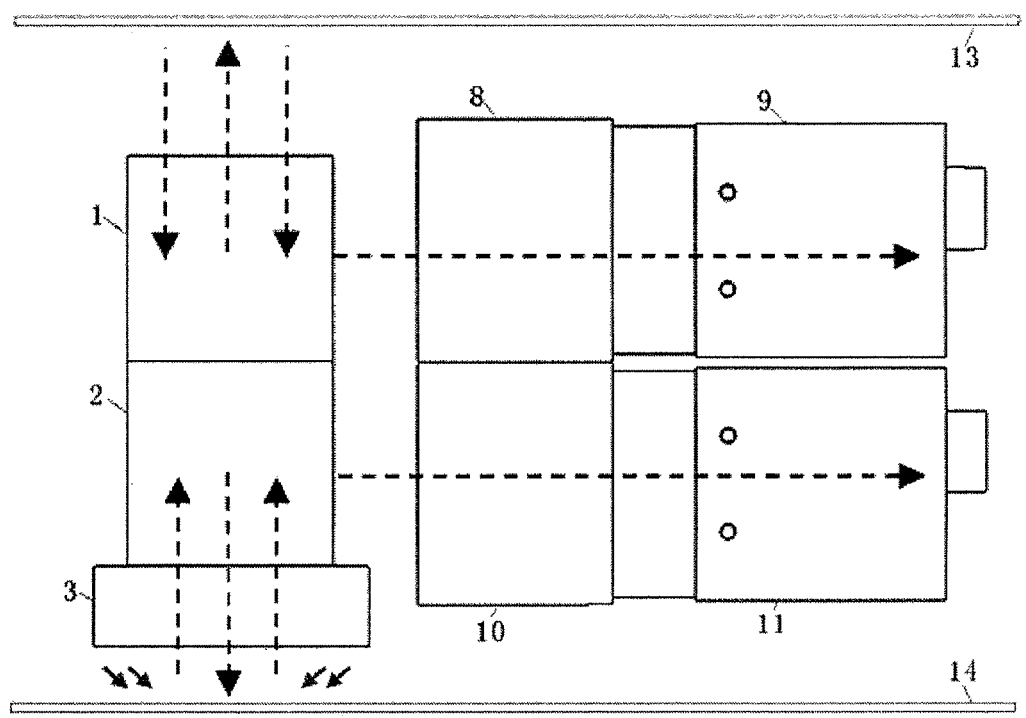
FIG. 3 is the front view of the imaging apparatus shown in FIG. 1 during operation.
Figure 4:
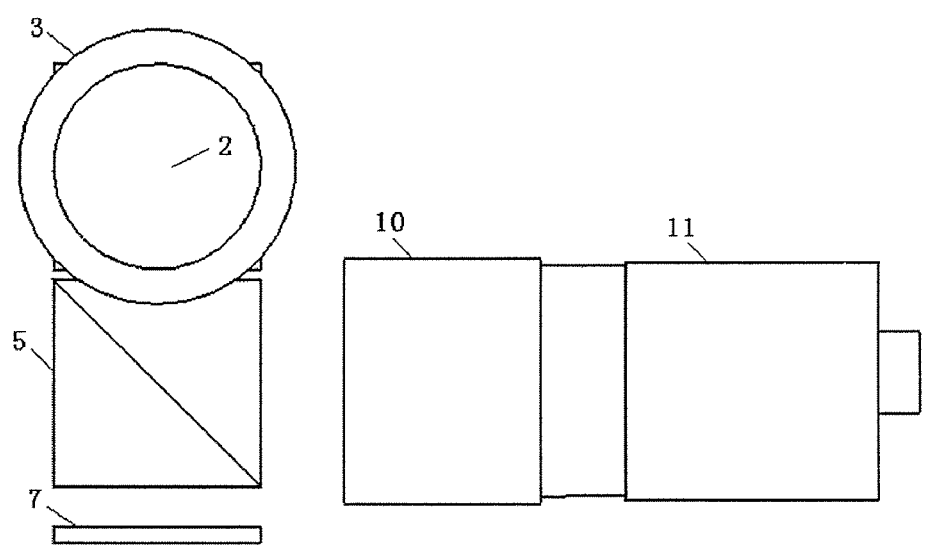
FIG. 4 is the bottom view of the imaging apparatus shown in FIG. 1.
Figure 5:
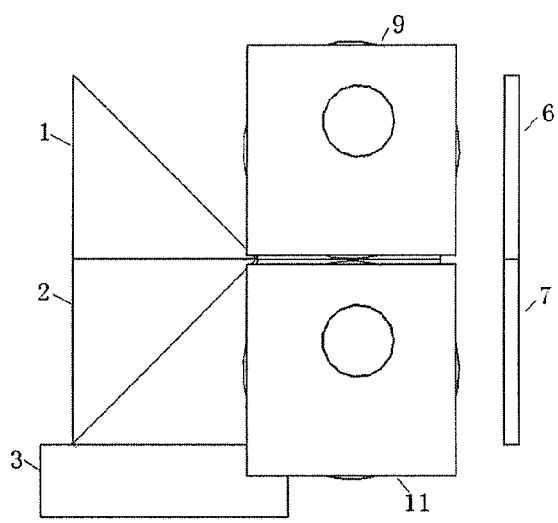
FIG. 5 is the right view of the imaging apparatus shown in FIG. 1.

Wherein,
1—the first reflector;
2—the second reflector;
3—low-angle LED ring light source;
4—the first beamsplitter;
5—the second beamsplitter;
6—the first LED light source;
7—the second LED light source;
8—the first imaging lens;
9—the first image sensor;
10—the second imaging lens;
11—the second image sensor;
12—imaging apparatus;
13—screen;
14—printed circuit board;
15—positioning device;
16—image acquiring control and processing device;

DETAILED DESCRIPTION OF THE INVENTION

The above characteristics and spirit of the present invention will be more clearly understood by the detailed description of the preferred embodiments accompanying the drawings, which are given as example only without intention to limit the protection scope of the present invention.

Embodiment 1

A T-type Imaging Apparatus with Two Lenses for Fully Automatic Screen Printer As shown in FIGS. 1, 2, 3, 4 and 5, the imaging apparatus for reference mark measurement and inspection of the solder-paste printing, includes a first reflector 1, a second reflector 2, a low-angle ring light source 3, a first beamsplitter 4, a second beamsplitter 5, a first LED light source 6, a second LED light source 7, a first imaging lens 8, a second imaging lens 10, a image sensor 9 and a second image sensor 10. The two stacked optical reflectors 1, 2 and the two stacked LED light sources 6, 7 are correspondingly disposed on two opposite sides of the two stacked beamsplitters 4, 5. The two stacked imaging lens 8, 10 are disposed on another side of the beamsplitters 4, 5 different from that of the optical reflectors and the light sources. The optical axes of the two stacked image sensors 8, 10 are orthogonal to that of the LED light sources 6, 7. The angles of the light-spitting planes of the two beamsplitters with respect to the axes of the two imaging lenses and the axes of the two light sources are both 45°. The beams of light from the first LED light source 6 and the second LED light source 7 are refracted to the first reflector 1 and the second reflector 2 by the first beamsplitter 4 and the second beamsplitter 5, respectively. Then, the beams of light are reflected to the screen 13 and the printed circuit board 14 by the first reflector 1 and the second reflector 2, respectively. The ring light source 3 is disposed below the reflector 2, so as to provide side illumination for the printed circuit board 14. The beam of light reflected downwards by the reflector 2 travels through the central hole of the ring light source 3 and irradiates on the printed circuit board 14. The reflected beams of light of the screen 13 are reflected in an angle of 90° towards the first beamsplitter 4 by the first reflector 1. The reflected beams of light of the printed circuit board 14 travel through the central hole of the ring light source 3 and then irradiate onto the second reflector 2 below, by which the beams of light are reflected back to the second beamsplitter 5. The first reflector 1 and the second reflector 2 are two isosceles right angle prisms stacked together. In the present embodiment, the first reflector 1 and the second reflector 2 may be two light-splitting plates or a right angle prism with two reflection planes. The first beamsplitter 4 and the second beamsplitter 5 are right angle prisms stacked together, or a cuboid beamsplitter, or one or two light-splitting plates. A part of the reflected light is refracted towards the first LED light source 6 and the second LED light source 7 by the first beamsplitter 4 and the second beamsplitter 5 respectively; the other part of the reflected light is reflected in an angle of 90° by the first beamsplitter 4 and the second beamsplitter 5 into the first imaging lens 8 and the second imaging lens 10, and then imaging is obtained on the first image sensor 9 and the second image sensor 11. The first image sensor 9 and the second image sensor 11 may be formed of analog CCD cameras or digital CCD cameras or CMOS cameras, so that the images are converted into analog signals or digital signals by the image sensors and transferred to computer for processing. In the whole imaging apparatus, the two stacked reflectors and the two stacked light sources are disposed on two opposite sides of the two stacked beamsplitters. The imaging apparatus forms a T-shaped structure, in which the upper light path and the lower light path are independent with respect to each other, and acquire the image of the screen and the image of the printed circuit board, respectively.

Figure 6:
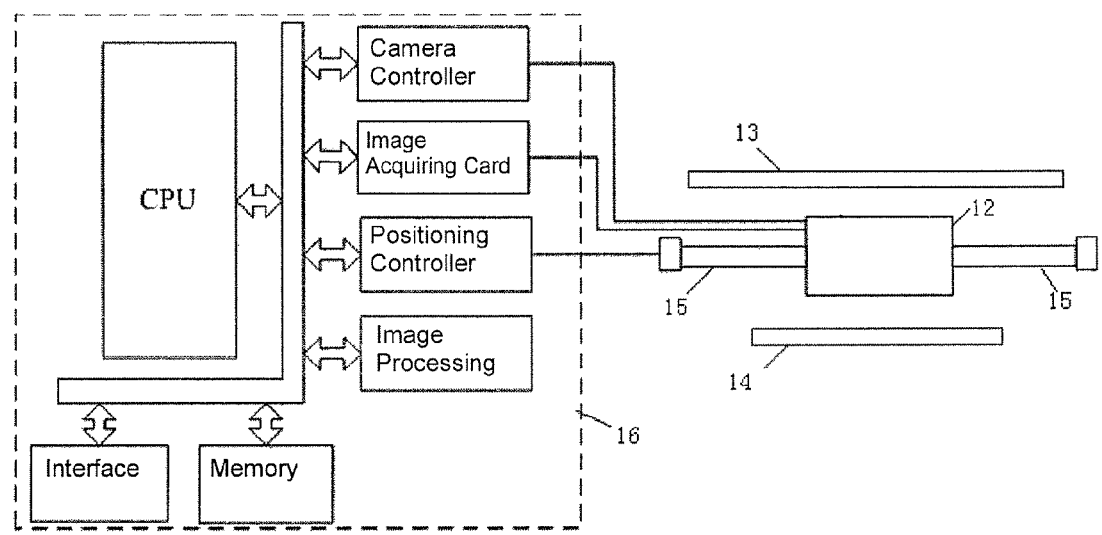
FIG. 6 is the schematic view showing the structure formed of the T-type imaging apparatus with two lenses as shown in FIG. 1, and the image acquiring control and processing device, along with the positioning device.

As shown in FIG. 6, in order to cooperate with the operation of the imaging apparatus according to the present invention, an image acquiring control and processing device 16 and a positioning device 15 are further required. The image acquiring control and processing device 16 consists of a camera controller, an image acquiring card, a positioning controller, an image processing model, a general computer and a memory. The camera controller is connected to the first LED light source 6, the second LED light source 7, the first image sensor 9 and the second image sensor 11 respectively, and controls the image acquiring of the first image sensor 9 and the second image sensor 11. The image acquiring card is connected to the video interfaces of the first image sensor 9 and the second image sensor 11, and the image video signals are converted into digital signals. The positioning controller is connected to the positioning device 15 on which the imaging apparatus 12 is mounted. When acquiring the images, according to the given coordinate information, the imaging apparatus 12 is conveyed to a designated position between the screen 13 and the printed circuit board 14. The imaging apparatus 12 simultaneously captures the image of the screen on the side facing the printed circuit board, and the image of the printed circuit board on the side facing the screen. The image acquiring process is automatically controlled and accomplished by program. The acquired images and the processing results are stored on the memory.

When using the imaging apparatus of this embodiment, the light emitted from the first LED light source 6 and the second LED light source 7 is refracted towards the first reflector 1 and the second reflector 2 by the first beamsplitter 4 and the second beamsplitter 5. A beam of light is reflected upwards to the screen 13 by the first reflector 1, while a beam of light is reflected downwards by the second reflector 2 and travels through the central hole of the ring light source 3 and irradiates onto the printed circuit board 11. The ring light source 3 provides side illumination for the image acquiring of the printed circuit board. The beam of light reflected back from the screen 10 is reflected towards the first beamsplitter 4 by the first reflector 1; the beam of light reflected back from the printed circuit board 14 travels through the central hole of the ring light source 3 and irradiates onto the second reflector 2, and then is reflected to the second beamsplitter 5. 50% of the light reflected back by the first reflector 1 and the second reflector 2 is refracted towards the first LED light source 6 and the second LED light source 7 by the first beamsplitter 4 and the second beamsplitter 5. The other 50% of the light is reflected in an angle of 90° towards the first imaging lens 8 and the second imaging lens 10 by the first beamsplitter 4 and the second beamsplitter 5, and finally the upper and lower paths of light are imaged on the first image sensor 9 and the second image sensor 10 separately.

When the imaging apparatus according to the embodiment of the present invention is used for reference mark measurement, the images of reference marks on the printed circuit board 14 and the screen 13 are simultaneously acquired, and then inputted into computer after being converted into digital signals by the image acquiring card, and the coordinates of the two reference marks can be calculated, and then deviation analysis is carried out, so that the alignment in high speed and high precision can be obtained.

When the imaging apparatus according to the embodiment of the present invention is used for the inspection of the solder paste printing, the images of the printed circuit board 14 and the screen 13 can be simultaneously acquired, and then inputted into computer after being converted into digital signals by the image acquiring card, and the digital signals are compared with the information of standard model stored on the computer, so that the block of the screen and the quality of solder-paste printing of the printed circuit board can be inspected.

Embodiment 2

A L-type Imaging Apparatus with Two Lenses for Fully Automatic Screen Printer

Figure 7:
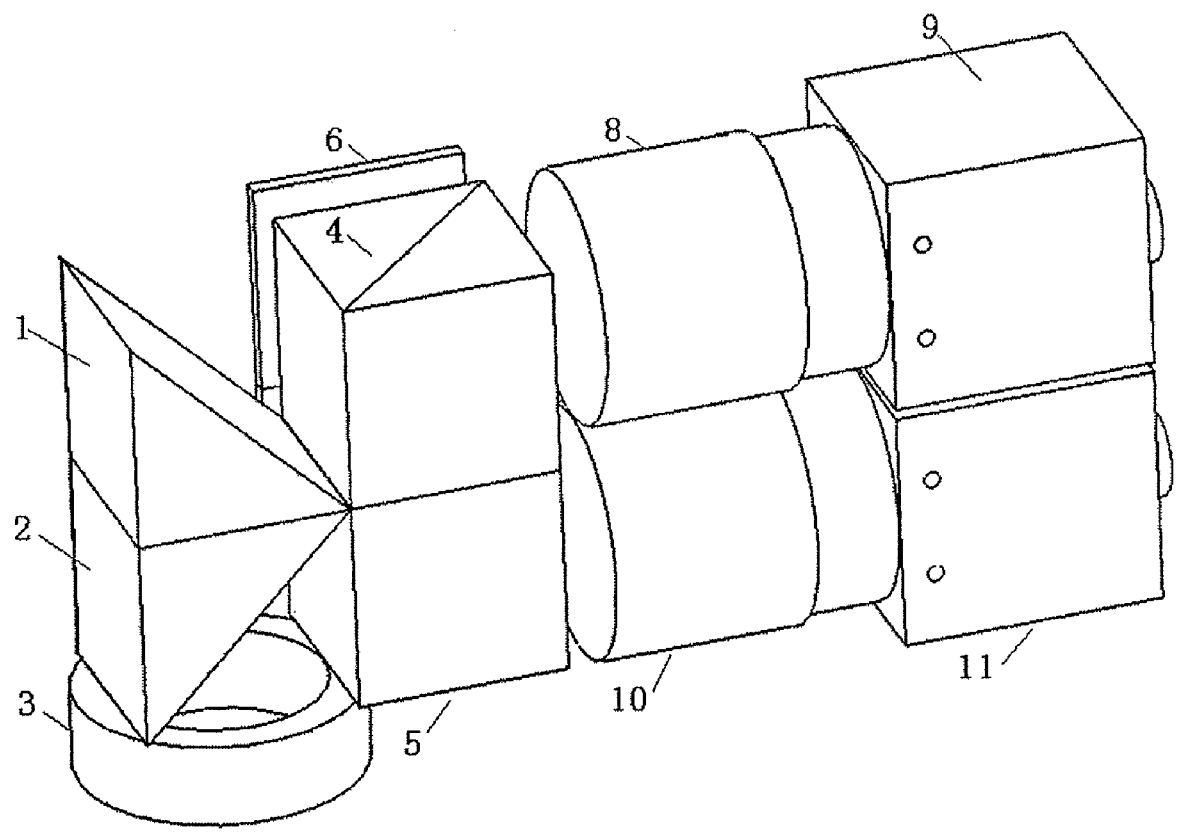
FIG. 7 is a schematic perspective view of the second embodiment showing a L-type imaging apparatus with two lenses for fully automatic screen printer.

As shown in FIG. 7, the two stacked reflectors 1, 2 and the two stacked imaging lenses 8, 10 are disposed on two opposite sides of the two stacked beamsplitters 4, 5, and the two stacked LED light sources 6, 7 are disposed on another side of the two stacked beamsplitters 4, 5 different from that of the reflectors and the imaging lenses, so that the imaging apparatus forms an L-shaped structure. The other features of the embodiment 2 are the same as that of the embodiment 1 as described above. The optical axes of the first imaging lens 8 and the second imaging lens 10 are both orthogonal to that of the first LED light source 6 and the second LED light source 7. The angles of the light-splitting planes of the two beamsplitters 4, 5 with respect to the axes of the two imaging lenses 8, 10 and the axes of the two LED light sources 6, 7 are both 45°.

The light emitted from the first LED light source 6 and the second LED light source 7 is reflected in an angle of 90° by the first beamsplitter 4 and the second beamsplitter 5 towards the first reflector 1 and the second reflector 2. Then, the beams of light are reflected towards the screen 13 and the printed circuit board 14 by the reflectors 1, 2, respectively. The ring light source 3 is disposed below the reflector 2, so as to provide side illumination for the printed circuit board 14. The beam of light reflected downwards by the reflector 2 travels through the central hole of the ring light source 3 and irradiates onto the printed circuit board 14. The beam of light reflected by the screen 13 is reflected in an angle of 90° towards the first beamsplitter 4 by the first reflector 1. The beam of light reflected by the printed circuit board 14 travels through the central hole of the ring light source 3 and then irradiates onto the second reflector 2 below, by which the beam of light is reflected back to the second beamsplitter 5. The first reflector 1 and the second reflector 2 are two isosceles right angle prisms stacked together. The reflectors also may be formed of two reflection mirror or a right angle prism with two reflection planes. A part of the reflected light from the screen 13 or the printed circuit board 14 is reflected in an angle of 90° by the first beamsplitter 4 and the second beamsplitter 5 towards the first LED light source 6 and the second LED light source 7; the other part of the reflected light is refracted into the first imaging lens 8 and the second imaging lens 10 by the first beamsplitter 4 and the second beamsplitter 5, and imaging is respectively obtained on the image sensor 9 and the image sensor 10. The images are converted by the image sensors into analog voltage signals or digital signals. The images are transferred to computer for processing.

The operation mode of the imaging apparatus according to this embodiment is the same as that of the embodiment 1.

The embodiments described above are only the preferred examples without intention to limit the protection scope of the present invention. Therefore, any amendments to the structure according to the present invention as described in the specification or the drawings are within the protection scope of the present invention.

We claim:

1. An imaging apparatus comprising:
   first and second stacked light sources;
   first and second stacked beamsplitters in optical communication with the first and second stacked light sources, respectively;
   first and second stacked optical reflectors in optical communication with the first and second stacked beamsplitters, respectively, and respectively provided with an upward reflection plane and a downward reflection plane; and
   first and second stacked imaging lenses in optical communication with the first and second stacked beamsplitters, respectively; and first and second stacked image sensors in optical communication with the first and second stacked beamsplitters, respectively, wherein the first and second stacked beamsplitters are each disposed on one side of the first and second stacked optical reflectors, and the first and second stacked light sources are each disposed on another side of the first and second stacked optical reflectors, and the first and second stacked imaging lenses are each disposed on another side of the first and second beamsplitters different from that of the first and second optical reflectors and the first and second light sources.

2. The imaging apparatus according to claim 1, wherein the upward reflection plane and the downward reflection plane are aligned at approximately a 90° angle with respect to one another.

3. The imaging apparatus according to claim 1, wherein the first and second beamsplitters are each formed of two right angle prisms.

4. The imaging apparatus according to claim 1, wherein at least one of the beamsplitters is formed of one or two light-splitting plates.

5. The imaging apparatus according to claim 1, wherein at least one of the optical reflectors includes an isosceles right angle prism, two reflection lenses, and a right angle prism with two reflection planes.

6. The imaging apparatus according to claim 1, wherein the image sensor includes at least one of an analog charge-coupled device (CCD) camera, a digital CCD camera, and a CMOS camera.

7. The imaging apparatus according to claim 1, further comprising:

a ring light source having a central hole and including a LED ring light source, the ring light source disposed between a printed circuit board and the optical reflector wherein at least one of the first and second optical reflectors is disposed relative to the at least one of the first and second light sources such that light emitted from the at least one of the first and second light sources travels through the central hole of the ring light source and then irradiates on the printed circuit board.

8. The imaging apparatus according to claim 1, further comprising an image acquiring control and processing device including a camera controller and an image acquiring card, wherein at least one of the light sources and the image sensors are connected to the camera controller so as to control the switching of at least one of the light sources and accordingly control image acquiring of a screen and printed circuit board to which light from the light source is ultimately directed; a video signal output end of at least one of the image sensors being connected to the image acquiring card so as to convert the acquired image video signals into digital signals.

9. The imaging apparatus according to claim 1, wherein the first and second stacked optical reflectors and the first and second stacked imaging lenses are correspondingly disposed on opposite sides of the first and second stacked beamsplitters, the first and second stacked light sources being disposed on another side of the first and second stacked beamsplitters different from the that of the first and second optical reflectors and the imaging lens to form an L-shaped structure.

10. The imaging apparatus according to claim 1, wherein the first and second light sources are disposed adjacent to one another.

11. The imaging apparatus according to claim 1, wherein optical axes of the first and second imaging lenses are substantially orthogonal to optical axes of the first and second light sources, respectively.

* * * * *